(12) United States Patent
Zink et al.

(10) Patent No.: US 10,287,553 B2
(45) Date of Patent: May 14, 2019

US010287553B2

(54) IN VITRO METHOD FOR CULTURING STEM CELLS

(71) Applicant: AGENCY FOR SCIENCE, TECHNOLOGY AND RESEARCH, Singapore (SG)

(72) Inventors: Daniele Zink, Singapore (SG); Ming Ni, Singapore (SG); Karthikeyan Narayanan, Singapore (SG); Karthikeyan Kandasamy, Singapore (SG); Andrew C. A. Wan, Singapore (SG); Jackie Y. Ying, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 17 days.

(21) Appl. No.: 14/395,811

(22) PCT Filed: Apr. 22, 2013

(86) PCT No.: PCT/SG2013/000160
§ 371 (c)(1),
(2) Date: Oct. 20, 2014

(87) PCT Pub. No.: WO2013/158048
PCT Pub. Date: Oct. 24, 2013

(65) Prior Publication Data
US 2015/0087057 A1 Mar. 26, 2015

Related U.S. Application Data

(60) Provisional application No. 61/636,157, filed on Apr. 20, 2012.

(51) Int. Cl.
*C12N 5/074* (2010.01)
*C12N 5/00* (2006.01)
*C12N 5/0735* (2010.01)
*C12N 5/0775* (2010.01)

(52) U.S. Cl.
CPC ......... *C12N 5/0696* (2013.01); *C12N 5/0068* (2013.01); *C12N 5/0075* (2013.01); *C12N 5/0606* (2013.01); *C12N 5/0663* (2013.01); *C12N 2500/90* (2013.01); *C12N 2501/815* (2013.01); *C12N 2531/00* (2013.01); *C12N 2533/00* (2013.01); *C12N 2533/20* (2013.01); *C12N 2533/30* (2013.01); *C12N 2533/50* (2013.01); *C12N 2533/70* (2013.01); *C12N 2533/78* (2013.01)

(58) Field of Classification Search
None
See application file for complete search history.

(56) References Cited

U.S. PATENT DOCUMENTS

| 8,257,828 | B2 | 9/2012 | McCarthy et al. | |
| 2012/0009159 | A1* | 1/2012 | Humayun | A61K 35/30 424/93.7 |
| 2012/0196345 | A1 | 8/2012 | Zink et al. | |
| 2013/0295669 | A1* | 11/2013 | Schenk | C12N 5/0606 435/375 |

OTHER PUBLICATIONS

Rim et al., Mussel-inspired surface modification of poly(L-lactide) electrospun fibers for modulation of osteogenic differentiation of human mesenchymalstem cells, Colloids and Surfaces B: Biointerfaces, vol. 91, 2012, pp. 189-197.*
Heng et al., Effect of Rho-associated kinase (ROCK) inhibitor Y-27632 on the post-thaw viability of cryopreserved human bone marrow-derived mesenchymal stem cells, Tissue and Cell 41 (2009) pp. 376-380.*
Ku et al., General functionalization route for cell adhesion on non-wetting surfaces, Biomaterials 31 (2010) pp. 2535-2541.*
Lonza, Poietics hMSC human mesenchymal stem cells & media, 2011, retrieved from the internet: http://bio.lonza.com/uploads/tx_mwaxmarketingmaterial/Lonza_BenchGuides_Poietics_hMSC_Human_Mesenchymal_Stem_Cells_Media.pdf.*
Mimura et al., Growth factor-defined culture medium for human mesenchymal stem cells, Int. J. Dev. Biol. 55: 181-187 (2011).*
Sigma Product Information, 3,4 Dihydroxy-L-phenylalanine, retrieved from the internet May 5, 2016: http://www.sigmaaldrich.com/content/dam/sigma-aldrich/docs/Sigma/Product_Information_Sheet/d9628pis.pdf.*
Wang et al., Enrichment of cancer stem cells by cotton fiber, RSC Advances., 2016, vol. 6, 23345.*
SigmaAldrich, Synthemax-R cell culture surface, retrieved from the internet: www.sigmaaldrich.com/labware/labware-products.html?TablePage=105745550.*
BSargent et al., The cell culture dish, retrieved from the internet, Feb. 21, 2018, http://cellculturedish.com/2011/04/a-critical-role-for-recombinant-albumin-in-embryonic-stem-cellips-cell-culture-and-therapeutic-development/.*
Ellerstrom et al., Stem Cells, 2006; 24: 21701-2176.*
Emre et al., PlosOne, Aug. 2010, vol. 5, Issue 8, pp. 1-10.*
Science Daily, Northwestern University, Sticky Mussels Inspsire Biomedical Engineer Yet Again, Oct. 20, 2007, pp. 1-4, retrieved from the internet: https://www.sciencedaily.com/releases/2007/10/071018142509.htm.*
Ludwig et al., Nature Biotechnology, vol. 24, No. 2, Feb. 2006, pp. 185-187.*
Kim et al., Increase of BM-MSC proliferation using L-DOPA on titanium surface in vitro, Journal of Biomaterials Applications (2011), vol. 27, No. 2, pp. 143-152.*

(Continued)

*Primary Examiner* — Thomas J. Visone
*Assistant Examiner* — Evelyn Y Pyla
(74) *Attorney, Agent, or Firm* — Womble Bond Dickinson (US) LLP

(57) ABSTRACT

There is provided a method for culturing a stem cell in vitro. The method comprises providing a substrate surface coated with a coating comprising a molecule having a catechol moiety or a polymer thereof; and growing a stem cell on said coated substrate surface in a growth medium.

14 Claims, 1 Drawing Sheet

(56) References Cited

OTHER PUBLICATIONS

Brafman, et al., "Long-term human pluripotent stem cell self-renewal on synthetic polymer surfaces," Biomaterials, vol. 31, Dec. 2010 (Epub Sep. 15, 2010), pp. 9135-9144.
Chen, et al., "Chemically defined conditions for human iPS cell derivation and culture", Nature Methods, vol. 8, No. 5, 2011 (Epub Apr. 10, 2011), pp. 424-429.
Derda, et al., "Defined substrates for human embryonic stem cell growth identified from surface arrays," ACS Chemical Biology, vol. 2, No. 5, 2007, pp. 347-355.
Derda, et al. "High-throughput discovery of synthetic surfaces that support proliferation of pluripotent cells," J Am Chem Soc, vol. 132, No. 4, Feb. 3, 2010 (Epub Jan. 12, 2010), pp. 1289-1295.
Gerecht, et al., "Hyaluronic acid hydrogel for controlled self-renewal and differentiation of human embryonic stem cells," Proc Natl Acad Sci U S A, vol. 104, No. 27, Jul. 3, 2007, pp. 11298-11303.
Harb, et al., "The Rho-Rock-Myosin signaling axis determines cell-cell integrity of self-renewing pluripotent stem cells," PLoS One, vol. 3, No. 8, Aug. 2008, e3001, pp. 1-13.
Hong, et al., "Hyaluronic acid catechol: A biopolymer exhibiting a pH-dependent adhesive or cohesive property for human neural stem cell engineering," Advanced Functional Materials, vol. 23, No. 14, Apr. 12, 2013 (Epub Nov. 7, 2012), pp. 1774-1780.
Hurley, et al., "Attachment of R28 stem cells to RCS eyecups treated with MAP derived peptides," Investigative Opthamology & Visual Science, vol. 46, 2005, E-abstract 4141.
Irwin, et al., "Engineered polymer-media interfaces for the long-term self-renewal of human embryonic stem cells," Biomaterials, vol. 32, No. 29, Oct. 2011 (Epub Jul. 20, 2011), pp. 6912-6919.
Kim, et al., "Increase of BM-MSC proliferation using L-DOPA on titanium surface in vitro," Journal of Biomaterials Applications, vol. 27, No. 2, Aug. 2012 (Epub Feb. 22, 2011), pp. 143-152.
Klim, et al., "A defined glycosaminoglycan-binding substratum for human pluripotent stem cells," Nature Methods, vol. 7, No. 12, Dec. 2010 (Epub Nov. 14, 2010), pp. 989-994.
Kolhar, et al., "Synthetic surfaces for human embryonic stem cell culture," Journal of Biotechnology, vol. 146, Apr. 1, 2010 (Epub Feb. 2, 2010), pp. 143-146.
Lai, et al., "Surface functionalization of TiO2 nanotubes with bone morphogenetic protein 2 and its synergistic effect on the differentiation of mesenchymal stem cells," Biomacromolecules, vol. 12, No. 4, Apr. 11, 2011 (Epub Mar. 7, 2011), pp. 1097-1105.
Li, et al., "Hydrogels as artificial matrices for human embryonic stem cell self-renewal," Journal of Biomedical Materials Research Part A, vol. 79, Oct. 5, 2006 (Epub Jun. 1, 2006), pp. 1-5.
Martin, et al., "Microcarriers and Their Potential in Tissue Regeneration," Tissue Engineering: Part B Rev., vol. 17, No. 1, Feb. 2011 (Epub Dec. 29, 2010), pp. 71-80.
Mei, et al., "Combinatorial development of biomaterials for clonal growth of human pluripotent stem cells," Nature Materials, vol. 9, 2010 (Epub Aug. 22, 2010), pp. 768-778.
Melkoumian, et al., "Synthetic peptide-acrylate surfaces for long-term self-renewal and cardiomyocyte differentiation of human embryonic stem cells," Nature Biotechnology, vol. 28, 2010 (Epub May 30, 2010), pp. 606-610.
Meng, et al., "Characterization of integrin engagement during defined human embryonic stem cell culture," The FASEB Journal, vol. 24, 2010 (Epub Nov. 20, 2009), pp. 1056-1065.
Nandivada, et al., "Fabrication of synthetic polymer coatings and their use in feeder-free culture of human embryonic stem cells," Nature Protocols, vol. 6, 2011 (Epub Jun. 23, 2011), pp. 1037-1043.
Ni et al., "Characterization of membrane materials and membrane coatings for bioreactor units of bioartificial kidneys," Biomaterials, vol. 32, No. 6, Feb. 2011 (Epub Dec. 9, 2010), pp. 1465-1476.
Ni, et al., "The use of a library of industrial materials to determine the nature of substrate-dependent performance of primary adherent human cells," Biomaterials, vol. 33, No. 2, Jan. 2012 (Epub Oct. 21, 2011), pp. 353-364.
Olivieri, et al., "Structural and Biophysical Characterization of a Cyclic Bioadhesive With Cell Attachment Ability," J Adhes., vol. 86, No. 1, Jan. 2010, pp. 111-130.
Poh, et al., "The effect of VEGF functionalization of titanium on endothelial cells in vitro," Biomaterials, vol. 31, No. 7, Mar. 2010 (Epub Dec. 5, 2009), pp. 1578-1585.
Rim, et al., "Mussel-inspired surface modification of poly(L-lactide) electrospun fibers for modulation of osteogenic differentiation of human mesenchymal stem cells," Colloids and Surfaces, B: Biointerfaces, vol. 91, Mar. 1, 2012 (Epub Nov. 6, 2011), pp. 189-197.
Villa-Diaz, et al., "Synthetic polymer coatings for long-term growth of human embryonic stem cells," Nature Biotechnolology, vol. 28, Jun. 2010 (Epub May 30, 2010), pp. 581-583.
Watanabe, et al., "A ROCK inhibitor permits survival of dissociated human embryonic stem cells," Nature Biotechnolology, vol. 25, Jun. 2007, pp. 681-686.
Yang, et al., "Polydopamine-mediated surface modification of scaffold materials for human neural stem cell engineering", Biomaterials, vol. 33, No. 29, Oct. 2012 (Epub Jul. 17, 2012), pp. 6952-6964.
International Report on Patentability dated Oct. 21, 2014 in corresponding PCT application No. PCT/SG2013/000160.
Written Opinion dated Aug. 21, 2015 in corresponding SG patent application No. 11201406622U.
Ludwig, et al., "Feeder-independent culture of human embryonic stem cells", Nature Methods, vol. 3, No. 8, (Aug. 24, 2006), pp. 637-646.
StemCell Technologies Inc., "Technical Manual: Maintenance of Human Pluripotent Stem Cells in mTeSR1", Version 4.1.0, (2015), pp. i-iv; 1-45.

\* cited by examiner

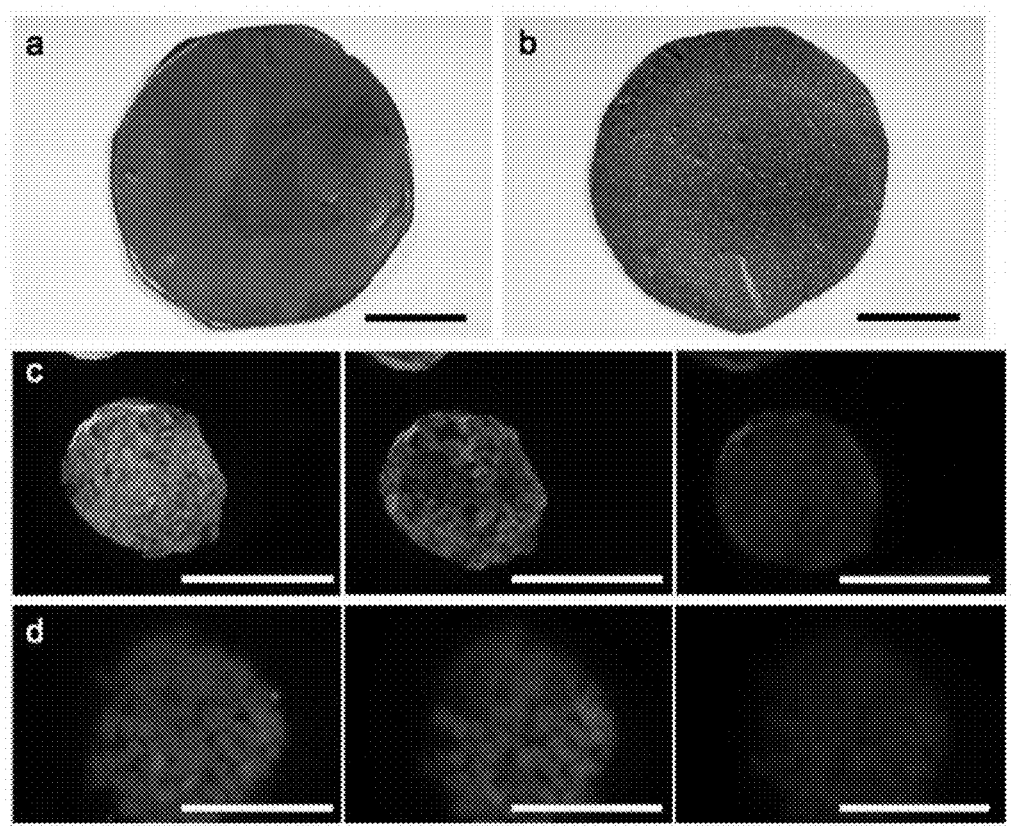

IN VITRO METHOD FOR CULTURING STEM CELLS

CROSS-REFERENCE TO RELATED APPLICATIONS

This patent application is a U.S. National Phase Application under 35 U.S.C. § 371 of International Application No. PCT/SG2013/000160, filed on Apr. 22, 2013, which claims benefit of, and priority from, U.S. provisional application No. 61/636,457, filed on Apr. 20, 2012, the contents of which were incorporated by reference.

FIELD OF THE INVENTION

The present invention relates to methods for culturing stem cells in vitro, including human stem cells.

BACKGROUND OF THE INVENTION

Pluripotent stem cells (PSCs), including human PSCs (hPSCs) and induced PSCs (iPSCs) are being examined as potential sources of cells for the treatment of a wide variety of diseases. Stem cells and cells differentiated or partially differentiated from such stem cells are also being explored for use in ex vivo tissue engineering and in vitro drug screening and toxicology studies.

The use of stem cells in commercial and clinical applications will require large-scale growth techniques that do not induce differentiation of the cell cultures (i.e. maintaining the stem cells under conditions of self-renewal).

Reliable methods for maintaining and expanding stem cells are of broad interest. In fact, for the success of potential clinical and industrial stem cell applications, it is absolutely essential to find conditions that allow production of large amounts of stem cells under defined conditions and at reasonable cost. This is not a trivial problem and satisfactory solutions are actively sought.

The commonly used feeder-free substrate for human pluripotent stem cells is Matrigel (BD), which is a poorly defined extracellular matrix (ECM) derived from mouse sarcomas. Therefore, there is a great interest in developing defined synthetic substrates to act as support for pluripotent and multipotent cells. Several synthetic substrates have been developed, and most contain recombinant peptides [1-10]. Such peptide-based substrates are expensive, which may make their use in large-scale expansion of stem cells cost-prohibitive.

In contrast, some less expensive substrates have been developed using synthetic chemical components and polymers. These synthetic substrates provide platforms that may be useful for industrial applications that require large numbers of stem cells in an undifferentiated or partially differentiated state. These synthetic substrates are based on aminopropylmethacrylamide (APMAAm) [11], poly[2-(methacryloyloxy)ethyl dimethyl-(3-sulfopropyl) ammonium hydroxide] (PMEDSAH [12, 13], and poly(methyl vinyl ether-alt-maleic anhydride) (PMVE-alt-MA) [14].

All three synthetic substrates (APMAAm, PMEDSAH and PMVE-alt-MA) were used with bovine serum albumin (BSA)-containing defined medium. In the case of APMAAm, it has been shown that BSA was critical for cell attachment. Attachment and proliferation of hESCs on this substrate was compromised as compared to Matrigel [11]. In the case of PMEDSAH, good results were only obtained with one of the 2 human embryonic stem cell (hESC) lines tested when defined media were used, and good results with the one cell line were only achieved with StemPro medium, but not with mTeSR1 medium[13].

Chen et al. (*Nat. Methods* 8(5), 424-429 (2011)) describes a completely defined albumin-free medium (E 8) containing 8 essential components. In the conditions described by Chen et al., the defined medium is used in conjunction with surfaces coated with recombinant vitronectin (vitronectin-N).

Polydopamine-coated polystyrene and poly-lactic-co-glycolic acid has been used for the proliferation and differentiation of human neural stem cells (Yang et al., *Biomaterials* 33(29), 6952-64).

The use of stem cells in industrial applications depends on the ability to design culture conditions that are chemically defined, robust, cost-effective and which may be devoid of animal-derived components, if desired.

SUMMARY OF THE INVENTION

In one aspect, the present invention provides a method for culturing a stem cell in vitro. The method comprises providing a substrate surface coated with a coating comprising a molecule having a catechol moiety or a polymer thereof; and growing a stem cell on said coated substrate surface in a growth medium.

The stem cell may be any stem cell, including a human stem cell or a non-human animal stem cell. The stem cell may be pluripotent or multipotent. The stem cell may be a tumor-initiating cell or a tumor stem cell. The stem cell may be an embryonic stem cell or an induced pluripotent stem cell. The stem cell may be an adult stem cell, including for example a mesenchymal stem cell.

The molecule having a catechol moiety may be, for example, 3,4-dihydroxy-phenylalanine (DOPA), including L-3,4-dihydroxy-phenylalanine (L-DOPA). In some embodiments, the coating comprises one or both of an L-DOPA monomer and a polymer thereof. The coating may optionally further comprise one or more of a protein, a peptide, a polysaccharide, a growth factor and a hormone, any of which may be a synthetic or recombinant molecule.

The growth medium may be entirely free from serum, including both human and non-human serum. The growth medium may contain serum, including human and/or non-human serum. The growth medium may be free from non-human serum but contain human serum, or may be free from human serum but contain non-human serum.

The growth medium may also be entirely free from animal components, including human and non-human animal components. Thus, the growth medium may be synthetic, containing synthetic or recombinant components that are not derived from animal cells or tissue, including for example one or more recombinant or synthetic proteins or peptides. The growth medium may include animal components, including human and/or non-human animal components. In some embodiments, the growth medium is free from non-human components, but may optionally contain one or more components derived from human blood, cells or tissue. In some embodiments, the growth medium is free from human components, but may optionally contain one or more components derived from non-human animal blood, cells or tissue.

In some embodiments, a ROCK inhibitor may be added to the growth medium during the growing of the stem cell.

The coated substrate surface may comprise glass, ceramic, metal, a polymer including natural or synthetic polymers, or a material having a nano-structured surface. In some embodiments, the coated substrate surface comprises a polymer comprising one or more of dextran, modified dextran, cross-linked amino-modified dextran, chitosan, chitin, cellulose, cellulose acetate, polylactic acid, aminopropylmethacrylamide, polysulfone, polystyrene, polyethylene, polyethersulfone, polyester, polycarbonate, polyethylene terephtalate, nylon, polytetrafluoroethylene, polypropylene, polyurethane, polyacrylamide, poly[2-(methacryloyloxy) ethyl dimethyl-(3-sulfopropyl) ammonium hydroxide], and poly(methyl vinyl ether-alt-maleic anhydride).

The substrate surface may be a cell culture vessel surface, a cell culture plate surface, a membrane surface or a micro-carrier surface.

Other aspects and features of the present invention will become apparent to those of ordinary skill in the art upon review of the following description of specific embodiments of the invention in conjunction with the accompanying FIGURES.

BRIEF DESCRIPTION OF THE DRAWINGS

The figures, which illustrate, by way of example only, embodiments of the present invention, are as follows.

In the FIGURE: Parts (a) and (b): The images show DOPA-coated polysulfone membranes (a) without and (b) with HUES7 cells. The membrane (b) was imaged 6 days after cell seeding. HUES7 cells formed colonies, which were uniformly distributed over the entire membrane area in (b). Scale bars: 5 mm. Parts (c) and (d): A colony formed by (c) HUES7 cells and (d) iPSCs. The HUES7 cells and iPSCs were cultured on DOPA-coated PSF for 6 days. The cell nuclei were stained with DAPI (blue) after immunostaining of OCT3/4 (green) and NANOG (red). Scale bars: (c) 200 μm and (d) 100 μm.

DETAILED DESCRIPTION

There are presently provided methods relating to in vitro culturing of stem cells. The methods provide for culturing of stem cells under conditions that allow for self-renewal and expansion of the stem cell cultures while discouraging or inhibiting any further differentiation of the stem cells.

The methods described herein are designed to provide culture conditions for self-renewal of undifferentiated stem cells and scalable expansion of undifferentiated stem cell cultures.

For scalable expansion of stem cells and related long-term passaging, finding conditions that allow for self-renewal of a population but that don't promote differentiation of the stem cells can be challenging. Finding such conditions is particularly important with respect to human stem cells, which are most relevant for clinical applications and other applications, for example in vitro toxicology assays.

Furthermore, if the stem cells are to be used for therapeutic applications, it is often desirable to have growth conditions that do not require any xeno components or factors, so as to minimise immunogenicity of the stem cell population and also to avoid potential cross-species disease transfer. For such applications, it may be desirable to have a well-defined system that uses synthetic components in order to minimize batch-to-batch variability.

Thus, in one aspect there is provided a method for culturing an animal stem cell in vitro. The method comprises providing a substrate surface for growing the stem cells on, the substrate surface coated with a coating comprising a molecule having a catechol moiety or a polymer thereof. The method further comprises growing the stem cell on the coated substrate surface in a growth medium. Growth conditions may be selected to maintain the level of differentiation of the stem cell or to maintain self-renewal in the undifferentiated state.

The term cell (including reference to a stem cell) as used herein refers to and includes a single cell, a plurality of cells or a population of cells where context permits, unless otherwise specified. Similarly, reference to cells also includes reference to a single cell where context permits, unless otherwise specified.

The stem cell used in the method may be any stem cell. For example, the stem cell may be from a non-human animal, or may be a human stem cell. The stem cell may be a pluripotent stem cell or may be a multipotent cell. The stem cell may be an embryonic stem cell, an adult stem cell or may be an induced pluripotent stem cell. The stem cell may be an adult stem cell that is partially differentiated and is a progenitor cell for a particular type of tissue or tissues, for example a mesenchymal stem cell or a tissue-specific stem cell. The stem cell may be a tumor stem cell, including a tumor cell that is multipotent, including for example a circulating tumor cell or a circulating tumor-initiating cell isolated from human body fluid. In various embodiments, the stem cell is a human embryonic stem cell, a human adult stem cell (including for example a human mesenchymal stem cell) or a human induced pluripotent stem cell. In various embodiments, the stem cell is a mesenchymal stem cell derived from adipose tissue, periosteum, synovial membrane, muscle, dermis, pericyte, blood, bone marrow or trabecular bone.

The substrate surface is selected to provide a suitable surface to support the growth and expansion of the stem cell in culture. The substrate surface is made from a material that can be coated with the coating, for example by adherence of the coating, grafting of the coating or covalent modification of the surface with the coating.

Thus, the substrate surface that is coated may be any surface that can be used as a solid support for stem cell growth. For example, the coated substrate surface may be a cell culture vessel surface, a cell culture plate surface, or a membrane or a micro-carrier surface.

The coated substrate surface may comprise a porous surface or a solid surface. Thus, for example, the substrate surface may comprise organic or inorganic materials, and may comprise for example glass, ceramic, metal, a polymer including a natural or synthetic polymer, or a material having a nano-structured surface.

In some embodiments, the coated substrate surface is a polymer. For example, the substrate surface may be a naturally derived polymer such as dextran including modified dextran such as cross-linked amino-modified dextran, chitosan, chitin, or cellulose including cellulose acetate.

In other examples, the polymer may be a synthetic polymer and may comprise one or more of polysulfone, polystyrene, polyethylene, polyethersulfone, polyester, polycarbonate, polyethylene terephtalate, nylon, polytetrafluoroethylene, polypropylene, polyurethane, polyacrylamide, polylactic acid, aminopropylmethacrylamide, poly[2-(methacryloyloxy)ethyl dimethyl-(3-sulfopropyl) ammonium hydroxide], or poly(methyl vinyl ether-alt-maleic anhydride).

The surface is coated with a coating composition that contains a molecule having a catechol moiety. The molecule having a catechol moiety may be a monomer that is subsequently polymerised, a polymer or a monomer or molecule that does not subsequently polymerise.

As will be appreciated, catechol is 1,2-dihydroxybenzene. Thus, a catechol moiety is any group that contains an ortho-substituted dihydroxyphenyl group.

In some embodiments, the molecule having a catechol moiety may be 3,4-dihydroxy-phenylalanine, for example L-3,4-dihydroxy-phenylalanine (L-DOPA). Thus, the coating may, in some embodiments, comprise or consist of an L-DOPA monomer and/or a polymer thereof.

In addition to the molecule having the catechol moiety, the coating may include other components that may encourage stem cell attachment or growth. For example, the coating may further comprise one or more of a protein, a peptide, a polysaccharide, a growth factor and a hormone.

If the growth conditions are desired to be free from animal components, the protein, the peptide, the polysaccharide, the growth factor or the hormone may be a synthetic or recombinant molecule and may be produced in a system that is free from any animal component, including any human component.

Alternatively, if the growth conditions are desired to be free from xeno components, the protein, the peptide, the polysaccharide, the growth factor or the hormone may be derived from the same species of animal, including humans, to which the stem cell is ultimately to be administered.

Reference to xeno components is reference to animal derived products that are from a different species of animal than that to which the stem cells are ultimately to be administered. It may also thus refer to components or products derived from a species of animal that is different from the species from which the stem cell is derived. For example, if the stem cell is to ultimately be used to treat a human in a therapeutic or clinical context, the stem cell may be a human stem cell, and any product or component that is not human derived (for example a protein isolated from mouse cells or tissue) would be considered a xeno component. Similarly, "xeno-free" is reference to a stem cell culture, stem cell growth substrate, stem cell growth medium or any component or product included in the stem cell culture that does not contain any xeno components.

The substrate surface is coated with the coating composition in such a manner that the molecule having a catechol moiety is located on the surface in order to present a catechol-modified surface to the stem cell for attachment and growth.

For example, the substrate surface may have the molecule having the catechol moiety adhered to it. Or the substrate surface may be chemically modified with the molecule having a catechol moiety, such that the molecule is conjugated to the substrate surface, including for example via a covalent bond. If the molecule is a polymer, the polymer may be grafted to or grafted from the substrate surface. Thus, in forming the coating on the substrate surface, a composition may be added to the surface that contains a monomeric molecule having a catechol moiety that is subsequently polymerised, or the composition may contain a polymeric molecule having a catechol moiety that is subsequently adhered to or conjugated to the substrate surface.

In one example, the molecule having a catechol moiety is DOPA, including for example L-DOPA, which may then further polymerise once added to the substrate surface.

In the method, the coated substrate surface is provided as a surface for stem cell attachment and growth. Thus, the stem cell is grown on the coated substrate surface. The coated substrate surface with the available catechol moiety allows for growth but does not induce differentiation of the stem cell. Thus, the coated surface sustains self-renewal and it is possible to grow stem cell cultures on the surface and maintain the same degree of differentiation or potency (i.e. pluripotency or multipotency) as is present in the original stem cell inoculum. That is, the potential for the stem cell to further differentiate is maintained. Thus, for pluripotent stem cells grown on the coated substrate surface, the expanded culture contains at least a majority of cells that remain pluripotent. For multipotent stem cells grown on the coated substrate surface, the expanded culture contains at least a majority of cells that maintain the multipotency and can potentially differentiate into the same types of cells as the initial stem cell inoculum. It will be appreciated that for any stem cell culture, the culture may contain a small number of cells that have differentiated, but the presence of such cells will not affect the overall nature of the stem cell population as pluripotent.

Growth media and conditions for growing stem cells are known. Growth media that allow for self-renewal and expansion of stem cells while maintaining the degree of undifferentiation are known.

For example, defined stem cell culture media include commercially available media such as mTeSR1 and TeSR2 (STEMCELL Technologies) and StemPro (Invitrogen). mTeSR1 contains bovine serum albumin and TeSR2 contains human serum albumin. Thus, with human stem cells, TeSR2 can be used when xeno-free conditions are required.

Depending on the desired end use of the stem cell culture, the stem cell growth medium may be serum-free or may comprise serum. If the growth medium includes serum, the serum may be selected so that the growth medium is still free from non-human serum, or alternatively, the growth medium may comprise non-human serum. The growth medium may comprise human serum or may be free from human serum.

However, in some embodiments, it may be desirable to use a serum-free medium, particularly in chemically defined media. That is, serum is a mix of different components and all the components may not be fully defined. In such cases, purified serum albumin may be included in some embodiments. In other embodiments, the growth medium may be free from serum and from serum albumin.

The growth medium may be free from human components, and thus may contain no human derived components, including any proteins derived from human blood, tissue or cells.

As well, or alternatively, the stem cell growth medium may be designed to be entirely free from non-human animal components. Thus, the growth medium may be free from non-human animal derived components, including any proteins derived from animal blood, tissue or cells.

Alternatively, depending on the stem cell type or desired ultimate use of the stem cell culture, the growth medium may further comprise one or more components derived from non-human animal blood or tissue.

If human stein cells are to be cultured in the method, and if the end use of the cultured stem cells is for clinical or therapeutic use in a human subject, the growth medium may comprise one or more components derived from human blood, cells or tissue.

The growth medium may comprise one or more recombinant or synthetic proteins or peptides. In one embodiment, the growth medium is synthetic and is free from animal components, including human and non-human animal components.

In the method, the stem cells are grown on the coated substrate surface and may attach to the surface.

The cells may be grown in accordance with standard stem cell culture methods, for a period of time and under conditions to expand the stem cell culture to the desired cell count, while maintaining the state of differentiation or non-differentiation of the original stem cell used to inoculate the culture. As indicated above, the coated substrate surface does not induce differentiation of the stem cells.

If desired, an inhibitor such as ROCK inhibitor may be added to the growth medium during the period during which the stem cell is cultured. For example, ROCK inhibitor may be added to the growth medium within 24 hours of seeding the stem cell onto the coated substrate surface. ROCK inhibitor encourages survival of diassociated embryonic stem cells. (Watanabe et al. Nat. Biotechnol.; 25, 681-686 (2007)).

Thus, the methods as described herein can be used to expand pluripotent and multipotent cells, including human cells, under defined and cost-effective conditions, using xeno-free conditions, if desired. Thus, the methods as described herein may be useful for the expansion of human stem cell cultures for use in industrial and large-scale in vitro cultures, for ultimate use in regenerative medicine, tissue engineering, drug screening and toxicology.

Compared to the industry standard Matrigel, as well as commercial peptide-based synthetic substrates currently used for stem cell cultures, DOPA coating is very inexpensive. A comparison of cost (priced in Singapore dollars (SGD), is shown in Table 1.

TABLE 1

| Material | Vendor | Source | Price (SGD) | Amount required per well (6 well plate) | Total cost for a 6 well plate (SGD) |
|---|---|---|---|---|---|
| DOPA (100 g) | Sigma-Aldrich | Synthetic | 420.00 | 10 mg | 0.25 |
| Polysulfone Membrane (8" × 11" sheet) | Pall Filtration | Synthetic | 35.57 | 10 cm$^2$ | 3.42 |
| Total cost (DOPA + PSF membrane) | | | | | 3.67 |
| Synthemax™ (2 plate/pack) | Corning | Synthetic Peptide | 114 | | 57 |
| Vitronectin-N (500 µg) | Life Technologies | Human recombinant truncated protein | 77.00 | 5 µg | 4.62 |
| Matrigel-ES qualified (5 ml) | BD Biosciences | Mouse tumor | 329.65 | 12.5 µl | 4.95 |

The present methods are further exemplified by way of the following non-limiting examples.

EXAMPLES

Example 1: Pluripotent Stem Cells

Experiments were conducted using hESCs and hiPSCs. 3 hESC lines were used: HUES7 and H1 cells (normal karyotype) and a hESC line from Invitrogen expressing the green fluorescent protein (GFP) under the Oct 4 promoter. GFP expression showed that the cells maintained their undifferentiated state, which would be important for long-term growth and large-scale expansion. iPSCs were generated by transfecting human fibroblasts with reprogramming proteins. In addition, commercial hiPSC lines were used with (hFIB2-iPS4, iPS IMR90-4 and iPSCs (Foreskin)-4) or without (DF19.9.11-T.H, DF6.9.9-T.B) vector/transgene sequences. The media used were mTeSR1, TeSR2 and E8 and MATRIGEL™ (a reconstituted basement membrane preparation) was used as a control substrate. When cells were seed on MATRIGEL™ or on the synthetic test substrate, ROCK inhibitor was added during day 1 (only) to promote cell attachment.

The synthetic test substrate used in these experiments consisted of commercial polysulfone membranes (PSF) (Pall, Ann Arbor, USA) soaked overnight in a solution containing 3,4-dihydroxy-L-phenylalanine (DOPA) (0.2 wt % DOPA in 10 mM Tris buffer, pH 8.5). During the soaking procedure, the membranes became coated by a dark melanin-like polymer formed by DOPA, which was easily recognized due to the color change of the membrane. PSF membranes were used for coating as this substrate was most efficiently modified as compared to other substrates (e.g. tissue culture polystyrene (TCPS)). However, DOPA may be used to coat or chemically modify a variety of different substrates that can be used in this method.

Initial experiments were performed with the hES-GFP cells (Invitrogen), which were seeded in parallel on MATRIGEL™-coated TCPS or DOPA-coated PSF. The results obtained demonstrated that cell attachment, growth and colony formation was similar on both substrates. Cells were grown for several passages, and the strong GFP fluorescence throughout the formed colonies indicated that almost all of the cells remained in the undifferentiated state. This was confirmed by immunostaining of the sternness markers, SOX2 and SSEA4.

Subsequently, similar experiments were performed with HUES7 and H1 cells. The cell attachment, growth and colony formation were similar on MATRIGEL™ and DOPA coatings (see the FIGURE, parts (a) and (b)). Cells were propagated for at least 10 passages in mTeSR1 medium, and analysed by immunostaining and flow cytometry. Immunostaining indicated robust expression of the sternness markers OCT3/4, NANOG, SSEA4, SOX2, TRA1-81 and TRA1-60 throughout the colonies at least up to passage 10 (see the FIGURE, part (c)). Flow cytometry analysis revealed that 98-99% of the cells still expressed the stemness markers TRA1-81, TRA1-60, OCT 3/4, NANOG, SOX2 and SSEA4 at passage number 10. After passage 10 teratoma assays performed with SCID mice confirmed pluripotency. Further, karyotype analyses revealed no abnormalities. Altogether, the results showed that hESCs can be propagated at normal growth rates on DOPA-coated PSF and maintained in an undifferentiated state.

Similar analyses were performed with all hiPSCs lines, which also showed uncompromised performance in terms of attachment, growth and colony formation on DOPA-coated membranes as compared to MATRIGEL™. iPSCs at passage numbers 1 and 10, showed robust expression of the stemness markers OCT 3/4, NANOG, SSEA4, SOX2, TRA1-81 and TRA1-60 throughout the colonies at both passages (see the FIGURE, part (d)). Flow cytometry analysis also revealed that iPSCs maintained expression of the stemness markers.

As no compromised cell performance was observed at the highest passage numbers (at least passage 10) there is no reason to believe that the cells could not be further propagated. Table 2 sets out the compiled results of immunostaining and flow cytometry of HUES7 cells and iPSCs grown on DOPA-PSF membranes at passage 1 and passage 10.

TABLE 2

| | HUES7 Passages | | iPSC Passages | |
|---|---|---|---|---|
| | 1 | 10 | 1 | 10 |
| Immunostaining | | | | |
| OCT3/4 | +++ | +++ | +++ | +++ |
| NANOG | +++ | +++ | +++ | +++ |
| SSEA4 | +++ | +++ | +++ | +++ |
| SOX2 | +++ | +++ | +++ | +++ |
| TRA1-81 | +++ | +++ | +++ | +++ |
| TRA1-60 | +++ | +++ | +++ | +++ |
| FACS | | | | |
| OCT3/4 | 94.40% | 99.9% | 99% | 99.8% |
| NANOG | 81% | 99.3% | ND | 99.2% |

Example 2: Mesenchymal Stem Cells

Human bone marrow-derived mesenchymal stem cells (hMSCs) were propagated on CYTODEX™ microcarriers (GE Healthcare). CYTODEX 1™ microcarriers comprise cross-linked dextran and are free of any animal or human products or recombinant proteins. CYTODEX 1™ microcarriers were used unmodified or after coating with DOPA as described for PSF membranes in Example 1. The microcarriers were incubated in the DOPA solution, and CYTODEX1™ microcarriers coated with CELLSTART™ (a commercial synthetic substrate) or fetal bovine serum (FBS) were used as controls. CYTODEX 3™ microcarriers (microcarriers coated with collagen were used as another control. The microcarrier cultures were conducted in STEMPRO™ medium.

The results indicated that hMSCs could grow under all conditions tested. Cell growth was similar on DOPA- and FBS-coated CYTODEX 1™ microcarriers. Under these conditions about 5-fold more cells were obtained on day 7 as compared to uncoated controls. Cell numbers on DOPA-coated microcarriers were about 2-fold higher than on CELLSTART™ coated CYTODEX 1™ microcarriers. Faster cell growth would be an advantage if large-scale expansion is required.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

REFERENCES

1. Derda R, Musah. S, Omer B P, Klim J R, Li L, Kiessling L L: High-throughput discovery of synthetic surfaces that support proliferation of pluripotent cells. *J Am Chem Soc* 2010, 132:1289-1295.
2. Klim J R, Li L, Wrighton P S, Piekarczyk M S, Kiessling L L: A defined glycosaminoglycan-binding substratum for human pluripotent stem cells. *Nat Methods* 2010, 7:989-994.
3. Mei Y, Saha K, Bogatyrev S R, Yang J, Hook A L, Kalcioglu Z I, Cho S W, Mitalipova M, Pyzocha N, Rojas F, et al: Combinatorial development of biomaterials for clonal growth of human pluripotent stem cells. *Nat Mater* 2010, 9:768-778.
4. Melkoumian Z, Weber J L, Weber D M, Fadeev A G, Zhou Y, Dolley-Sonneville P, Yang J, Qiu L, Priest C A, Shogbon C, et al.: Synthetic peptide-acrylate surfaces for long-term self-renewal and cardiomyocyte differentiation of human embryonic stem cells. *Nat Biotechnol* 2010, 28:606-610.
5. Meng Y, Eshghi S, Li Y J, Schmidt R, Schaffer D V, Healy K E: Characterization of integrin engagement during defined human embryonic stem cell culture. *Faseb J* 2010, 24:1056-1065.
6. Kolhar P, Kotamraju V R, Hildta S T, Clegg D O, Ruoslahti E: Synthetic surfaces for human embryonic stem cell culture. *J Biotechnol* 2010, 146:143-146.
7. Gerecht S, Burdick J A, Ferreira L S, Townsend S A, Langer R, Vunjak-Novakovic G: Hyaluronic acid hydrogel for controlled self-renewal and differentiation of human embryonic stem cells. *Proc Natl Acad Sci USA* 2007, 104:11298-11303.
8. Li Y J, Chung E H, Rodriguez R T, Firpo M T, Healy K E: Hydrogels as artificial matrices for human embryonic stem cell self-renewal. *J Biomed Mater Res A* 2006, 79:1-5.
9. Harb N, Archer T K, Sato N: The Rho-Rock-Myosin signaling axis determines cell-cell integrity of self-renewing pluripotent stem cells. *PLoS One* 2008, 3:e3001.
10. Derda R, Li L, Omer B P, Lewis R L, Thomson J A, Kiessling I L: Defined substrates for human embryonic stem cell growth identified from surface arrays. *ACS Chem Biol* 2007, 2:347-355.
11. Irwin E F, Gupta R, Dashti D C, Healy K E: Engineered polymer-media interfaces for the long-term self-renewal of human embryonic stem cells. *Biomaterials* 2011, 32:6912-6919.
12. Nandivada H, Villa-Diaz L G, O'Shea K S, Smith G D, Krebsbach P H, Lahann J: Fabrication of synthetic polymer coatings and their use in feeder-free culture of human embryonic stem cells. *Nat Protoc* 2011, 6:1037-1043.
13. Villa-Diaz L G, Nandivada H, Ding J, Nogueira-de-Souza N C, Krebsbach P H, O'Shea K S, Lahann J, Smith G D: Synthetic polymer coatings for long-term growth of human embryonic stem cells. *Nat Biotechnol* 2010, 28:581-583.
14. Brafman D A, Chang C W, Fernandez A, Willert K, Varghese S, Chien S: Long-term human pluripotent stem cell self-renewal on synthetic polymer surfaces. *Biomaterials* 2010, 31:9135-9144.

15. Kim S H, Park J K, Hong J H, Jung H S, Hong K S, Lee J H, Park K B, Choi S K, Seo Y K: Increase of BM-MSC proliferation using L-DOPA on titanium surface in vitro. *J Biomater Appl.* 2011, Epub ahead of print.
16. Ni M, Teo J C, Ibrahim M S, Zhang K, Tasnim F, Chow P Y, Zink D, Ying J Y: Characterization of membrane materials and membrane coatings for bioreactor units of bioartificial kidneys. *Biomaterials* 2011, 32:1465-1476.

What is claimed is:

1. An in vitro method for expanding a pluripotent stem cell by self-renewal while maintaining the level of differentiation of the stem cell, the method comprising:
providing a substrate surface coated with a coating comprising L-3,4-dihydroxy-phenylalanine (L-DOPA); and
growing a pluripotent stem cell attached on said coated substrate surface in a growth medium under growth conditions that do not induce differentiation of the stem cell for at least 10 passages.

2. The method according to claim 1, wherein the pluripotent stem cell is a human pluripotent stem cell.

3. The method according to claim 1, wherein the pluripotent stem cell is a non-human animal pluripotent stem cell.

4. The method according to claim 1, wherein the L-DOPA comprises one or both of an L-DOPA monomer and an L-DOPA polymer.

5. The method according to claim 1, wherein the coating further comprises one or more of a protein, a peptide, a polysaccharide, a growth factor and a hormone.

6. The method according to claim 5, wherein the protein, the peptide, the polysaccharide, the growth factor or the hormone is a synthetic or recombinant molecule.

7. The method according to claim 1, wherein the growth medium:
(a) is free from non-human serum;
(b) is free from non-human animal components; or
(c) comprises one or more components derived from non-human animal blood, cells or tissue.

8. The method according to claim 7, wherein the growth medium comprises non-human serum.

9. The method according to claim 1, wherein the growth medium:
(a) is free from human serum;
(b) is free from human components; or
(c) comprises one or more components derived from human blood, cells or tissue.

10. The method according to claim 1, wherein the growth medium comprises human serum.

11. The method according to claim 1, wherein the growth medium is synthetic and is free from animal components, including human and non-human animal components.

12. The method according to claim 1, wherein the growth medium comprises one or more recombinant or synthetic proteins or peptides.

13. The method according to claim 1, wherein the pluripotent stem cell is an embryonic stem cell or an induced pluripotent stem cell.

14. The method according to claim 1, wherein said growing comprises adding Rho-associated kinase (ROCK) inhibitor to the growth medium.

* * * * *